United States Patent [19]  [11] 4,414,127
Fu  [45] Nov. 8, 1983

[54] CONTACT LENS CLEANING SOLUTIONS

[75] Inventor: Cherng-Chyi Fu, Sunnyvale, Calif.

[73] Assignee: Syntex (U.S.A.) Inc., Palo Alto., Calif.

[21] Appl. No.: 280,035

[22] Filed: Jul. 6, 1981

[51] Int. Cl.$^3$ .......................... C11D 9/42; D06L 3/00; B08B 7/00
[52] U.S. Cl. .......................... 252/95; 134/42; 252/98; 252/102; 252/186.38; 252/542; 252/545; 252/546; 252/186.41; 252/186.42
[58] Field of Search .................... 252/90, 95, 99, 102, 252/186, 542, 545, 546, 98; 134/42

[56] References Cited

U.S. PATENT DOCUMENTS

| | | | |
|---|---|---|---|
| 3,499,844 | 3/1970 | Kibbel et al. | 252/102 X |
| 3,884,826 | 5/1975 | Phares et al. | 252/106 |
| 3,908,680 | 9/1975 | Krezanoski | 134/42 X |
| 3,912,451 | 10/1975 | Gaglia | 134/42 X |
| 4,013,576 | 3/1977 | Loshack | 252/106 |

*Primary Examiner*—Michael R. Lusignan
*Attorney, Agent, or Firm*—Howard M. Peters; Joseph I. Hirsch; James M. Kanagy

[57] ABSTRACT

Disclosed herein are aqueous solutions for cleaning contact lenses comprising a water-soluble peroxide, transition metal salts, an amphoteric or anionic surfactant, and, optionally, tonicity salts.

29 Claims, No Drawings

CONTACT LENS CLEANING SOLUTIONS

BACKGROUND

1. Field of the Invention

This invention discloses solutions for cleaning plastic contact lense materials. Specifically it relates to aqueous solutions comprising a water-soluble peroxide, a catalytic amount of a transition metal salt, a surfactant, and optionally, a tonicity salt. These solutions effectively clean hard, flexible and soft hydrogel contact lenses.

Because of the environment in which contact lenses are handled and employed, a wide variety of materials may adhere to lenses. During wear, lenses are subjected to proteinaceous materials, particularly lysozymes and mucoproteins; and lipids such as sterols, waxes, glycerides, phospholipids, fatty alchols and acids. In addition to these naturally occurring materials, cosmetics, greases from the hands and dusts and other airborne and environmental materials can all act to form a strongly adhering lens coating.

Proteinaceous materials constitute the major amount of lens soils. They can also be difficult to remove completely and efficiently from plastic lens materials, particularly in the instance of hydrophilic hydrogel materials which can readily absorb lysozyme and mucoproteins. If lenses are not properly cleaned these proteinaceous materials and other soils can build up to a point where wearer comfort is affected, lens spectral characteristics are affected, sterilization becomes difficult or gas permeability may be decreased.

Physical characteristics of the various lens plastics vary widely, ranging from the structurally rigid, lipophilic, polymethyl methacrylate (PMMA) and PMMA-silicone materials to the flexible, hydrophilic, hydrogel polymers. Rigid polymerics can be mechanically scrubbed even though it may be most desirable to keep handling to a minimum to avoid scratching, breaking or otherwise mechanically damaging the lenses. Hydrogel polymers and other soft flexible lens materials cannot be mechanically scrubbed because they are easily torn or scratched. Therefore some non-mechanical means must be used to remove soil accretions.

Additionally, lenses must be sterilized to prevent transmission of pathogenic agents onto the eye. Certain lens polymers, particularly hydrogels, cannot be chemically sterilized because they absorb antimicrobial drugs which are also eye irritants, so alternative sterilization techniques such as heat in the form of boiling water or steam are often used. High temperatures don't clean lenses and in fact tend to accelerate lens soil buildup by precipitating absorbed proteinaceous materials. Sterile saline solutions have little if any effect on soil removal so some additional cleaning procedure is required. Peroxides alone are adequate disinfectants but do not adequately remove lens soils, particularly non-polar materials.

It is therefore desirable to find a simple and efficient one step procedure for cleaning contact lenses which will ensure the removal of all soils but especially proteinaceous material. The procedure should be usable with all contact lenses. The method should be effective over a relatively short period of time, certainly not longer than overnight, and should be safe to the user and provide a clean lens which may be readily rinsed and safe for introduction into the eye thereafter without further treatment.

2. Prior Art

Contact lens cleaning solutions utilizing peroxides are disclosed in U.S. Pat. Nos. 3,873,696, 3,829,329, 3,908,608 and British Pat. No. 2,03,03. Bleaching and cleaning solutions containing similar ingredients are set out in U.S. Pat. Nos. 3,991,000, 3,583,924, and 2,975,139. Contact lens cleaning solutions which utilize surfactants, particularly amphoteric surfactants, are disclosed in U.S. Pat. Nos. 4,104,187, 4,126,587, and 4,046,706.

SUMMARY OF THE INVENTION

Solutions are provided for cleaning contact lenses. When finally formulated for use, these solutions are aqueous cleaning compositions which comprise a water-soluble peroxide; a catalytic amount of a transition metal in the form of an inorganic or organic salt; a surfactant which is a monocarboxylated, dicarboxylated or sulfonated, fatty acid substituted imidazoline amphoteric surfactant, a sulfonated amido-amine amphoteric surfactant or a coco-hydrolyzed animal protein anionic surfactant; and optionally, a tonicity salt.

Secondly this invention regards an article of manufacture comprising two packages from which aliquots are combined to make a contact lens cleaning composition wherein one package contains a granular or aqueous peroxide and the other contains an aqueous solution comprising a transition metal in the form of an inorganic or ogranic salt; a surfactant which is a monocarboxylated, dicarboxylated or sulfonated, fatty acid substituted imidazoline amphoteric surfactant, a sulfonated amido-amine amphoteric surfactants or a coco-hydrolyzed animal protein anionic surfactant; and optionally, a tonicity salt. Working solutions are prepared just prior to use by combining, in predetermined ratios, aliquots from the two separately provided containers.

In yet another aspect this invention relates to a process for cleaning contact lenses which process comprises contacting a contact lens with a solution comprising a peroxide; a catalytic amount of a transition metal in the form of an inorganic or organic salt; a surfactant which is a monocarboxylated, dicarboxylated or sulfonated, fatty acid substituted imidazoline amphoteric surfactant, a sulfonated amido-amine amphoteric surfactantsor a coco-hydrolyzed animal protein anionic surfactant; and optionally, a tonicity salt.

DESCRIPTION OF THE INVENTION

Compositions provided herein are effective for cleaning all types of contact lens plastics. These compositions affect all lens soils but are particularly effective in degrading and removing proteinaceous deposits which constitute the major amount of soil collecting on contact lenses. Because these compositions work primarily by chemically degrading proteinaceous soils into water-soluble peptides, mechanical lens manipulation is not needed or recommended. Elevated temperatures are not involved so the risk of thermal hardening of proteins or other soils is much reduced.

These compositions can be used to clean soft hydrogel lenses as well as other soft, flexible or so called hard lenses. Lenses treated with these solutions on a regular basis can be kept free of protein deposits. Sebaceous materials and other oil and fat based soils are also solubilized during the cleaning process. Routine use of these solutions will serve to maintain wearer comfort, retain lens spectral characteristics and extend the life of the lens. Since lens handling during cleaning is deminimus, fragile lens materials may be thoroughly cleaned without added concern for the lens' physical integrity.

Disclosed compositions are water-based solutions containing peroxides, metal salts and surfactants, with tonicity salts added if desired. Peroxides, catalyzed to active oxygen by the included metal ions, act to remove proteinaceous soils by hydrolytically degrading proteins into water-soluble fragments. Surfactants assist in the solubilization of peroxide degraded proteins, prevent redeposition of solubilized soils, and act to remove lipids, sterols and other waxy lens accretions.

Proteinaceous soil removal action is primarily derived from the hydrolytic or proteolytic action of water-soluble peroxides. More specifically, proteins and proteinaceous materials are degraded into amino acids and low molecular weight polypeptides by the action of a highly reactive oxygen species, variously described as active oxygen or perhydroxy radicals, on peptide linkages. This highly reactive radical species is generated from the peroxides by means of a catalytic amount of transition metal ion. Active oxygen readily hydrolyzes peptide bonds, thus reducing water-insoluble high molecular weight proteins to their water-soluble precursor amino acids and peptides.

While most any inorganic or organic peroxy containing compounds have the potential for acting as a source of active oxygen, this invention utilizes low molecular weight, water-soluble inorganic or carbon-containing peroxides. Preferred peroxides are hydrogen peroxide, sodium perborate, sodium percarbonate, and urea peroxide. Hydrogen peroxide and sodium perborate are most preferred.

Peroxides alone are relative stable. However in the presence of certain catalyticly active chemicals, peroxides rapidly undergo the oxidation-reduction reaction which generates the active oxygen species. Transition metal ions such as those included in this invention act as such catalysts. Mixing peroxides and such transition metals results in an immediate initiation of the active oxygen generating reaction. Since this reaction ends only when all peroxides have been consumed, if peroxide and catalyst were to be combined in a single container at the point of formulation, such compositions would have no hydrolytic activity by the time they reached the intended user. According, packages separately containing peroxides and metal ion catalyst must be prepared.

Peroxides may be packaged as solutions or, where appropriate, as powders. In the practice of this invention the most preferred peroxides, hydrogen peroxide and sodium perborate, are respectively provided as aqueous solutions and in powder form.

Efficient and effective cleaning solutions can be achieved with these peroxides when they are present in an amount between 0.1 and 15% by weight/volume (w/v) but preferably in an amount between 0.5% and 10% (w/v). Most preferred is a peroxide concentration of 1%. It should be understood that these concentrations refer to the solution concentrations at the time such solutions are finally prepared for cleaning contact lenses.

The proteolytic and mucolytic activities of these compositions are essentially dependent on the presence of certain transition metal which catalyze active oxygen production from peroxides.

The transition metals which may be used as catalysts in these compositions are, for example, cobalt, maganese, nickle, chromium, molybdenum or copper, each in its highest oxidation state.

The particular chemical form in which these metal ions are made available to the system is not of importance so long as the chemical entity is completely soluble in the solution at the required concentrations. It is preferred to use organic or inorganic salts of these various metals, but most preferbly inorganic salts will be used. Organic anions which may be used are, for example, formate, acetate, propionate, lactate, oxalate, butyrate or the like. Inorganic anions which may be used are, for example, fluoride, chloride, bromide, sulfate, nitrate, orthophosphate, borate or the like.

Copper is the most preferred transition metal for the compositions set out herein. Copper may be added in any of the salt forms described above, provided the chosen compound has the requisite water solubility. Inorganic salts are preferred. The most preferred source is copper sulfate ($CuSO_4$).

Since the transition metal is a catalyst, only a very small amount is needed to generate active oxygen. Because weights of metal salts will vary widely depending upon the particular metal and its salt, molar concentrations, rather than weight per volume figures, are recited so that amounts of metal can be uniformly expressed. For the purposes of this invention a catalytically effective amount of transition metal is an amount between 0.25 micromoles and 0.25 millimoles per deciliter. Metal concentrations between 2.5 micromoles and 0.25 millimoles per deciliter are preferred but most preferred is a concentration of 15 micromoles per deciliter. These figures refer to actual lens cleaning compositions, not concentrations in shelf packages.

Since copper is the most preferred metal and copper sulfate is the most preferred form, concentrations by weight/volume for the latter are set out for purposes of convenience. An effective catalytic amount of copper, expressed as copper sulfate, would be an amount between 0.0001% and 0.1% (w/v), but preferably the copper sulfate will be present in an amount of about 0.006% (w/v), again stated with reference to actual cleaning solutions.

It has been found that adding certain surfactants, particularly amphoteric and certain anionic surfactants, complements the peroxide's hydrolytic activity by aiding in the removal hydrolyzed protein fragments from the lens; and ensuring soils do not recollect on the lens during storage should they be left in the cleaning solution for extended periods. The presence of these surfactants also serves to effectively remove sebaceous deposits and other oil-based substances which may have accumulated from cosmetic and environmental sources and which are not affected by the hydrolytic activity of active oxygen.

While a surfactant could be chosen from a broad spectrum of anionic, cationic, nonionic, or amphoteric surfactants, it is preferred to use an amphoteric surfactant or certain anionic surfactants. The preferred amphoterics are monocarboxylated, dicarboxylated or sulfonated, aliphatic fatty acid substituted imidazoline compounds and sulfonated, fatty acid amido-amine compounds.

The preferred imidazoline surfactants have the general formula:

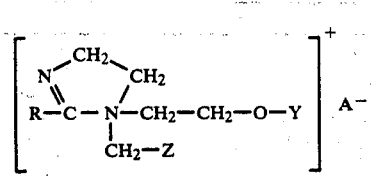

Formula I wherein:
R is a saturated or unsaturated aliphatic acid radical of 8 to 20 carbon atoms;
Y is hydrogen or a group having the formula —CH$_2$COOM or —CH$_2$CH$_2$COOM;

Z is —COOM, —CH$_2$COOM or —CHOHCH$_2$SO$_3$M wherein M is sodium, hydrogen or an organic ammonium radical; and
A is hydroxide, chloride or sulfate.

Organic ammonium radicals suitable for use with these imidazoline-based amphoteric surfactants include ammonium, amines, or alcohol or alkylol amines such as, for example, mono, di and triethanolamine and mixtured thereof, propanolamines, butanolamines; polynitrogenous amines such as ethylene diamine, ethylene triamine and the like, pyridine, methylpyridine, piperidine; quaternary ammonium bases such ar tetraethyl ammonium hydroxide, tetramethyl ammonium hydroxide; and in general, primary, secondary and tertiary amines substituted or not with other radicals such as hydroxy, alkyl, aryl, cycloalkyl groups, and the like.

Procedures for making such compounds and related compounds can be found in U.S. Pat. Nos. 2,781,349; 2,781,350; 2,781,351; 3,231,580; 3,231,581; 3,452,042; 3,658,985; and 3,697,452.

Preferred compounds of the above formula are the dicarboxylates wherein Y is CH$_2$COOM, Z is COOM, R is an aliphatic acid radical derived from coconut oil, lauric acid, capric acid, caprylic acid, ethylhexoic acid, linoleic acid or mixtures thereof; and M is sodium. Most preferred is the compound wherein the aliphatic acid radical forming substituent is coconut oil, Y is —CH$_2$COOM, Z is —COOM, M is sodium and A is hydroxide. This preferred compound is identified as AMPHOTERIC-2 in the CTFA Cosmetic Ingredient Dictionary (1976 Ed.). It is commercially available as Miranol ® C2M concentrate from the Miranol Chemical Co., Inc.

A second preferred amphoteric surfactant is a sulfonated fatty amido-amine compound having the formula:

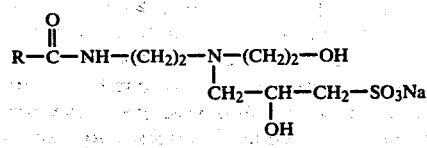

Formula II wherein R is an unbranched aliphatic chain having 16 carbons with 1 unsaturation site, that being a double bond between carbons 8 and 9. This surfactant is identified in the CTFA Cosmetic Ingredient Dictionary (1976 ED.) as AMPHOTERIC-7. It is commercially available from Sandoz Colors and Chemicals, Co. under the name Sandopan ® TFL Concentrate.

A third preferred surfactant is an anionic surfactant prepared by condensing coconut oil with certain hydrolyzed animal proteins. It has the general formula:

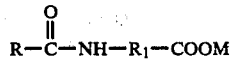

Formula III wherein R is a polypeptide; R$_1$ is a long-chain saturated or unsaturated aliphatic radical; and M is an alkali metal such as sodium, potassium, or magnesium or an organic amine such as mono, di or triethanol amine.

These surfactants are produced by subjecting animal protein such as skin and connective tissue to extensive hydrolysis resulting in the formation of low molecular weight polypeptides. Since this reaction does not produce peptides of a single molecular weight or peptide sequence, no single molecular weight or amino acid sequence is assigned to the hydrolysis product. Rather, it is expressed in terms of a particular molecular weight range. Polypeptides fallng into a particular weight range are then acylated to give compounds of Formula III by various acylating agents such as fatty acid halides, hydrides, acyl carbonates, and the like. Characteristics of a particular surfactant will be determined both by the polypeptide's average molecular weight as well as the acylating agent employed to form the surfactant.

The preferred surfactant of this type is the one in which R is a fatty acid radical obtained from coconut oil, R$_1$ is a polypeptide and M is an alkali metal. Most preferred are those surfactants of Formula III wherein R is derived from coconut oil, R$_1$ is a polypeptide derived from collagen having an average molecular weight of 250, and M is potassium. This surfactant is identified in the CTFA Cosmetic Ingredient Dictionary (1976 Ed.) as Stepan 4C. It is available commercially from the Stepan Chemical Co. as Maypon ® 4C.

The amount of surfactant used in formulations of these compositions is independent of which surfactant is employed. While a surfactant may be present in an amount of about 0.1 to 20% by weight/volume (w/v), a preferred amount would between 1 and 10% but most preferably around 1%, calculated in reference to the solution as finally prepared and used for cleaning lenses.

One or more recited surfactants may be included in a particular formulation. However the preferred practice of this invention will use only one surfactant.

These solutions may also contain other ingredients which assist in making them compatible with eye tissue. For example, various solutes may be added to the composition to adjust the tonicity so that it is comparable with that of eye tissue and eye fluid. Polyols such as glycols or low molecular weight polyethylene glycols and the like may be added to adjust the tonicity. Salts such as alkali, metal halides can also be added for this purpose. These metal halide salts may be, for example, sodium chloride, sodium bromide, potassium bromide, potassium chloride or potassium fluoride. Solutes may be added in an amount which will approximate the osmotic pressure equivalent to a sodium chloride content of between 0.5% and 1.8%, preferably 0.9% (w/v).

The materials of this invention may be packaged in any manner so long as the peroxide and heavy metal ion salt are not placed in the same container. A preferred method would be to make the peroxide available in one container as an aqueous solution or as a granular powder and provide all the other ingredients as an aqueous solution in a second container. Cleaning solutions would then be prepared just prior to use by combining aliquots of predetermined size from each container; and then immediately immersing a lens in this solution. Subsequent rinsing of the lens before inserting a lens onto the eye is recommended.

Aliquots of any size from either container could be combined so long as the resulting solution contained concentrations for the respective components in accordance with the various ranges set out above and hereinafter.

As matter of convenience, where the peroxide is prediluted in water, it is preferred to combine equal quantities of solution from each container to achieve working composition. Under this scheme, stock solutions would be prepared at twice the concentrations required in the working compositions. Thus aqueous peroxide solutions would be prepared in a range from 0.2 to 30% (w/v) while its complementary solution would contain 0.50 micromoles to 0.50 millimoles transition metal per deciliter, 0.2 to 40% (w/v) of surfactant, and optionally 1.0 to 3.6% (w/v) tonicity salts. Preferably aqueous peroxide solutions would contain 1.0 to 20% (w/v) of peroxide and the complementary solution would contain 5.0 micromoles to 0.05 milimoles per deciliter of transition metal, 1.0 to 20% (w/v) of surfactant and optionally 1.4 to 2.4% (w/v) of tonicity salts. It is most preferred to prepackage concentrations, aqueous peroxide solutions at a concentration of 2% (w/v) peroxide. Its complementary preparation would contain 30 micromoles of heavy metal ion, (0.012% (w/v) copper sulfate), 2% (w/v) surfactant, and 1.8% (w/v) tonicity salts.

Where granular peroxides such as sodium perborate are used, the complementary aqueous solution would contain the other ingredients at strengths which parallel the concentration ranges of finally prepared cleaning solutions as outlined above. Granular peroxides are most preferably combined with their complementary aqueous solutions to form lens cleaning solutions in a ratio of 1.2 parts by weight of peroxide to 1 volume of solution.

For a clear understanding of the invention, specific examples are set forth below. All percentages refer to weight/volume measurements.

EXAMPLE 1

A solution of 2% hydrogen peroxide solution, component A, and a separate aqueous mixture of 0.012% copper sulfate, 2% Maypon ® 4C, and 1.8% sodium chloride, component B, were prepared. Immediately prior to use, equal volumes of component A and B were mixed. The final solution contained 1% hydrogen peroxide, 0.006% copper sulfate, 1% Maypon ® 4C, and 0.9% sodium chloride.

To test the utility of latter compositions, contact lenses were artificially soiled with two protein solutions containing different types of protein. The first solution was comprised of the following:

| SOLUTION I | |
|---|---|
| lysozyme | 0.1% |
| NaH$_2$PO$_4$ | 0.06% |
| Na$_2$HPO$_4$ | 0.01% |
| QS H$_2$O | 100%. |

The second solution contained

| SOLUTION II | |
|---|---|
| mucin (porsine stomach) | 0.2% |
| albumin (bovine) | 0.394% |
| lysozyme (egg white) | 0.214% |
| alpha globulin (bovine) | 0.065% |
| beta and gamma globulin (bovine) | 0.188% |
| calcium chloride | 0.04% |
| sodium chloride | 0.798% |
| QS H$_2$O | 100%. |

A Contact lens (soft hydrogel lens of Corneal Science, Inc., Polycon lens, and conventional hard lens) was soiled by soaking it in one protein solution for thirty minutes then drying it in a laminar flow hood for one hour or longer. The process was repeated several times in the same protein solution until an opaque, white film coated the lenses. The lens was then put in an 80°–90° C. water bath for a period of thirty minutes.

Following this treatment, the lens was individually soaked in the cleaning composition, prepared by combining equal volumes of components A and B described above, for a period of time somewhere between two and four hours. The lenses were then rinsed with water and examined by means of a microscope. Each type of lens mentioned was processed through each protein solution.

Proteinaceous deposits of both types were satisfactorily removed from all lenses tested. Cleanliness and optical clarity were markedly improved for all lenses, but particularly for the soft hydrogel lenses.

EXAMPLE 2

In this example, as in Example 1, two solutions were prepared, one containing 2% aqueous hydrogen peroxide and the other containing 0.012% copper sulfate, 2% Sandopan ® TFL Conc. and 1.8% sodium chloride. Contact lenses were artificially soiled as described in Example I and then immersed in a cleaning composition prepared by combining equal volumes of the two solutions described in this Example. After two to four hours, lenses were removed from the cleaning solution and thoroughly rinsed with water. Inspection with a microscope revealed all proteinaceous deposits were completely removed from the several contact lenses tested.

EXAMPLE 3

In this example, granular sodium perborate was substituted for hydrogen peroxide as a source of active oxygen. In this instance, component A comprised granular sodium perborate and component B comprised an aqueous solution of 0.012% copper sulfate, 1% Miranol ® C2M concentrate, and 0.9% sodium chloride. Immediately prior to use, 0.24 grams of the sodium perborate were added to 20 ml of component B to provide the cleaning solution. Lenses soiled with protein as described in Example 1 were soaked in this solution for up to four hours, at which time all proteinaceous material had been removed as determined by microscopic inspection.

These examples are set out to illustrate the actual working of this invention and are in no way meant to be exhaustive of the various combinations which may be prepared from the information set out in the above specifications. Nor are they intended to limit the scope of the practice of this invention. The scope of this invention is determined finally by the content of the claims.

What is claimed is:

1. An aqueous contact lens cleaning composition which comprises
   a water-soluble peroxide;
   a catalytic amount of a water soluble transition metal catalyst in the form of an inorganic or organic salt;
   a surfactant which is (a) a monocarboxylated, dicarboxylated or sulfonated, fatty acid substituted imidazoline amphoteric surfactant, (b) a sulfonated amido-amine amphoteric surfactant or, (c) a coco-hydrolyzed animal protein anionic surfactant.

2. The composition of claim 1 which contains
   0.1% to 15% by weight/volume (w/v) of said peroxide;
   0.25 micromoles to 0.25 millimoles per deciliter of said metal;
   0.1% to 20% (w/v) of said surfactant; and
   water in a quantity sufficient to make volume.

3. The composition of claim 2 wherein
   said peroxide is hydrogen peroxide, sodium perborate, urea peroxide or sodium percarbonate;
   said metal is copper, manganese, nickel, cobalt, chromium or molybdenum in the form of an inorganic salt; and
   said surfactant is an amphoteric surfactant represented by the formula

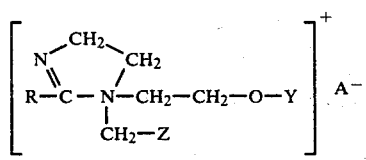

Formula I wherein:
R is a saturated or unsaturated aliphatic acid radical of 8 to 20 carbon atoms;
Y is hydrogen or a group having the formula —CH₂COOM or —CH₂CH₂COOM;

Z is —COOM, —CH₂COOM or —CHOHCH₂SO₃M wherein
M is sodium, hydrogen or an organic ammonium radical; and
A is hydroxide, chloride or sulfate.

4. The composition of claim 3 which contains
   0.5% to 10% by weight/volume (w/v) of said peroxide;
   2.5 micromoles to 0.025 millimoles per deciliter of said metal;
   0.5% to 10% (w/v) of said surfactant; and
   water in a quantity sufficient to make volume.

5. The composition of claim 4 wherein
   said peroxide is granular sodium perborate;
   said metal is copper, in the form of copper sulfate;
   said surfactant is the compound according to Formula I wherein R is coconut oil, Y is —CH₂COOM, Z is —COOM, M is sodium and A is hydroxide.

6. The composition of claim 5 which contains 1% (w/v) of said peroxide; 15 micromoles per deciliter of said metal (0.006% (w/v) of copper sulfate); 1% (w/v) of said surfactant; and water sufficient to make volume.

7. The composition of claim 2 wherein
   said peroxide is hydrogen peroxide, sodium perborate, urea peroxide or sodium percarbonate;
   said metal is copper, manganese, nickel, cobalt, chromium or molybdenum in the form of an inorganic salt; and
   said surfactant is an amphoteric surfactant represented by the formula

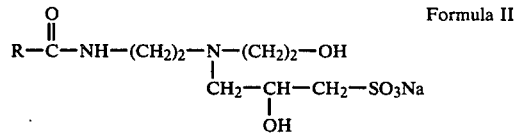

Formula II wherein R is an unbranched aliphatic chain having 16 carbons with 1 unsaturation site, that being a double bond between carbons 8 and 9.

8. The composition of claim 7 which contains
   0.5% to 10% by weight/volume (w/v) of said peroxide;
   2.5 micromoles to 0.025 millimoles per deciliter of said metal;
   0.5% to 10% (w/v) of said surfactant; and
   water in a quantity sufficient to make volume.

9. The composition of claim 8 wherein
   said peroxide is hydrogen peroxide;
   said metal is copper, present as copper sulfate;
   said surfactant is the compound according to Formula II.

10. The composition of claim 9 containing 1% (w/v) of said peroxide; 15 micromoles per deciliter of said metal (0.006% (w/v) of copper sulfate); 1% (w/v) of said surfactant; and water sufficient to make volume.

11. The composition of claim 2 wherein
    said peroxide is hydrogen peroxide, sodium perborate, urea peroxide or sodium percarbonate;
    said metal is copper, manganese, nickel cobalt, chromium or molybdenum in the form of an inorganic salt; and
    said surfactant is an anionic surfactant represented by the formula

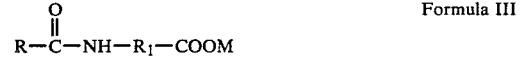

Formula III wherein R is a a long-chain saturated or unsaturated aliphatic radical, R₁ is a polypeptide, and M is an alkali metal such as sodium, potassium, or magnesium or an organic amine such as mono, di or triethanol amine.

12. The composition of claim 11 which contains
    0.5% to 10% by weight/volume (w/v) of said peroxide;
    2.5 micromoles to 0.025 millimoles per deciliter of said metal;
    0.5% to 10% (w/v) of said surfactant; and
    water in a quantity sufficient to make volume.

13. The composition of claim 12 wherein
    said peroxide is hydrogen peroxide;
    said metal is copper, in the form of copper sulfate;
    said surfactant is a compound according to Formula III wherein R is derived from coconut oil, R₁ is a collagen derived polypeptide of average molecular weight 250, and M is potassium.

14. The composition of claim 13 containing 1% (w/v) of said peroxide; 15 micromoles per deciliter of said metal (0.006% (w/v) of copper sulfate); 1% (w/v) of said surfactant; and water sufficient to make volume.

15. An article of manufacture comprising two packages from which aliquots are combined to make a contact lens cleaning composition wherein
one package contains a granular or aqueous peroxide and the other contains an aqueous solution comprising
a catalytic amount of water soluble transition metal catalyst in the form of an inorganic or organic salt;
a surfactant which is (a) a monocarboxylated, dicarboxylated or sulfonated, fatty acid substituted imidazoline amphoteric surfactant, (b) a sulfonated amido-amine amphoteric surfactants or (c) a coco-hydrolyzed animal protein anionic surfactant.

16. The article of claim 15 wherein one package contains
a granular peroxide or an aqueous peroxide solution having a concentration of 0.2% to 30% (w/v) and the second package contains
0.25 micromoles to 0.50 millimoles per deciliter of said metal;
0.1% to 40% (w/v) of said surfactant;
and water in a quantity sufficient to make volume.

17. The article of claim 16 wherein
said peroxide is hydrogen peroxide, sodium perborate, urea peroxide or sodium percarbonate
said metal is of copper, manganese, nickel, cobalt, chromium or molybdenum present in the form of an inorganic salt; and
said surfactant is an amphoteric surfactant represented by the formula

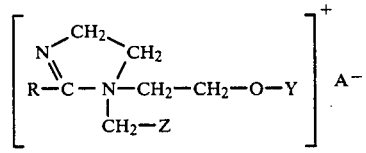

Formula I wherein:
R is a saturated or unsaturated aliphatic acid radical of 8 to 20 carbon atoms;
Y is hydrogen or a group having the formula —CH$_2$COOM or —CH$_2$CH$_2$COOM;

Z is —COOM, —CH$_2$COOM or —CHOHCH$_2$SO$_3$M wherein M is sodium, hydrogen or an organic ammonium radical; and A is hydroxide, chloride or sulfate.

18. The article of claim 17 wherein
one package contains a granular peroxide or an aqueous peroxide at a concentration of 0.5% to 20% (w/v) and the other contains an aqueous solution comprising
2.5 micromoles to 0.050 millimoles per deciliter of said metal;
0.5% to 20% (w/v) of said surfactant;
and water in a quantity sufficient to make volume.

19. The article of claim 18 wherein
said peroxide is granular sodium perborate;
said metal is copper, present as copper sulfate;
said surfactant is the compound according to Formula I wherein the fatty acid forming substituent is coconut oil, Y is CH$_2$COOM, Z is COOM, M is sodium and A is hydroxide.

20. The article of claim 19 wherein
one package contains said granular peroxide and the other package contains an aqueous solution comprising
15 micromoles per deciliter of said metal (0.006% (w/v) of copper sulfate);
1% (w/v) of said surfactant; and
water sufficient to make volume there being 0.12 units by weight of said peroxide mixed with 10 units by volume of said aqueous solution to make a contact lens cleaning composition.

21. The article of claim 16 wherein
said peroxide is hydrogen peroxide, sodium perborate, urea peroxide or sodium percarbonate;
said metal is copper, iron, manganese, nickel, cobalt, chromium or molybdenum present in the form of an inorganic salt; and
said surfactant is an amphoteric surfactant represented by the formula

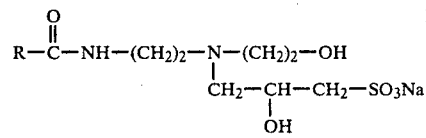

Formula II wherein R is an unbranched aliphatic chain having 16 carbons with 1 unsaturation site, that being a double bond between carbons 8 and 9.

22. The article of claim 21 wherein
one package contains granular peroxide or aqueous peroxide at a concentration of 0.2% to 20% (w/v) and the second package contains
0.25 micromoles to 0.50 millimoles per deciliter of said metal;
0.5% to 20% (w/v) of said surfactant; and
water in a quantity sufficient to make volume.

23. The article of claim 22 wherein said peroxide is aqueous hydrogen peroxide; said metal is copper, in the form of copper sulfate; and said surfactant is the compound according to Formula II.

24. The article of claim 23 wherein
one package contains 2% (w/v) of said peroxide and the other contains
30 micromoles per deciliter of said metal (0.012% (w/v) of copper sulfate);
2% (w/v) of said surfactant; and
water sufficient to make volume.

25. The article of claim 16 wherein
said peroxide is hydrogen peroxide, sodium perborate, urea peroxide or sodium percarbonate;
said metal is copper, manganese, nickel, cobalt, chromium or molybdenum present in the form of an inorganic salt; and
said surfactant in an anionic surfactant
represented by the formula

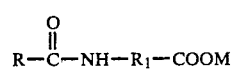

Formula III wherein R is a long-chain saturated or unsaturated aliphatic radical R$_1$ is a polypeptide and M is an alkali metal such as sodium, potassium, or magnesium or an organinc amine such as mono, di or triethanol amine.

26. The article of claim 25 wherein one package contains granular peroxide or an aqueous peroxide solution having a concentration of 0.5% to 20% (w/v) and the other package contains 2.5 micromoles to 0.050 millimoles per deciliter of said metal;

0.5% to 20% (w/v) of said surfactants; and water in a quantity sufficient to make volume.

27. The article of claim 26 wherein said peroxide is aqueous hydrogen peroxide; said metal is copper, in the form of copper sulfate; and said surfactant is the compound according to Formula III wherein R is derived from coconut oil, $R_1$ is a collagen derived polypeptide of average molecular weight 250, and M is potassium.

28. The article of claim 27 wherein one package contains 2% (w/v) of said peroxide and the other contains 30 micromoles per deciliter of said metal (0.006% (w/v) of copper sulfate);

1.8% (w/v) of said tonicity salt;

2% (w/v) of each said surfactant; and water sufficient to make volume there being a contact lens cleaning solution prepared by mixing equal volumes from each package.

29. A process for cleaning contact lenses which process comprises contacting a contact lens with a solution comprising a peroxide; a catalytic amount of a water soluble transition metal catalyst in the form of an inorganic or organic salt; and a surfactant which is (a) a monocarboxylated, dicarboxylated or sulfonated, fatty acid substituted imidazoline amphoteric surfactant, (b) a sulfonated amido-amine amphoteric surfactants (c) or a coco-hydrolyzed animal protein anionic surfactant.

* * * * *